US012150742B1

(12) United States Patent
Fong et al.

(10) Patent No.: US 12,150,742 B1
(45) Date of Patent: Nov. 26, 2024

(54) HAND-HELD APPARATUS FOR NONINVASIVE MEASUREMENT OF A HEART PERFORMANCE METRIC

(71) Applicant: Verily Life Sciences LLC, South San Francisco, CA (US)

(72) Inventors: Shannon Fong, San Francisco, CA (US); Eric Bennett, San Carlos, CA (US); Brian Derek DeBusschere, Los Gatos, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 386 days.

(21) Appl. No.: 17/684,957

(22) Filed: Mar. 2, 2022

Related U.S. Application Data

(60) Provisional application No. 63/160,148, filed on Mar. 12, 2021.

(51) Int. Cl.
*A61B 5/021* (2006.01)
*A61B 5/00* (2006.01)
(Continued)

(52) U.S. Cl.
CPC ........ *A61B 5/02141* (2013.01); *A61B 5/0205* (2013.01); *A61B 5/02241* (2013.01); *A61B 5/097* (2013.01); *A61B 5/7425* (2013.01); *A61B 5/7475* (2013.01); *A61B 2560/0456* (2013.01); *A61B 2562/0247* (2013.01)

(58) Field of Classification Search
CPC .............. A61B 5/02141; A61B 5/0205; A61B 5/02241; A61B 5/097; A61B 5/7425; A61B 5/7475; A61B 2560/0456; A61B 2562/0247
See application file for complete search history.

(56) References Cited

U.S. PATENT DOCUMENTS 3,776,221 A  12/1973 McIntyre
3,908,639 A   9/1975 McIntyre
(Continued)

FOREIGN PATENT DOCUMENTS

WO    2020046942 A1    3/2020

OTHER PUBLICATIONS

Bernardi, L., et al., "Do Hemodynamic Responses to the Valsalva Maneuver Reflect Myocardial Dysfunction?" Chest 95:986-991, 1989.
(Continued)

*Primary Examiner* — Bo Joseph Peng
(74) *Attorney, Agent, or Firm* — Christensen O'Connor Johnson Kindness PLLC

(57) ABSTRACT

Apparatuses, machine-accessible storage media, and methods for noninvasively measuring a heart performance metric, such as left ventricular filling pressure, are described. In an embodiment, the apparatus includes a housing shaped to be grasped by a hand; a tower protruding from a surface of the housing positioned to conform to a finger of the hand when grasping the housing; a tactile sensor disposed on a curved surface of the tower and adapted to measure blood pressure pulsatility in a digital artery of the finger and output pulsatility signals indicative of the blood pressure pulsatility; a graphical user interface for orchestrating a test of the performance metric of the heart and displaying results of the test.

16 Claims, 17 Drawing Sheets

(51) Int. Cl.
    *A61B 5/0205*   (2006.01)
    *A61B 5/022*    (2006.01)
    *A61B 5/097*    (2006.01)

(56) References Cited

U.S. PATENT DOCUMENTS

| | | | |
|---|---|---|---|
| 5,291,895 | A | 3/1994 | McIntyre |
| 6,610,018 | B1 | 8/2003 | McIntyre |
| 7,404,800 | B2 | 7/2008 | McIntyre |
| 9,549,678 | B2 | 1/2017 | Silber |
| 2006/0195020 | A1* | 8/2006 | Martin .................. G16H 40/63 600/595 |
| 2007/0021672 | A1 | 1/2007 | Lee et al. |
| 2007/0055163 | A1* | 3/2007 | Asada .................. A61B 5/6838 600/490 |
| 2012/0123232 | A1* | 5/2012 | Najarian ................ G16Z 99/00 600/407 |
| 2014/0107497 | A1 | 4/2014 | Semler et al. |
| 2015/0272455 | A1* | 10/2015 | Krasnov .............. A61B 5/6826 600/490 |
| 2017/0224349 | A1* | 8/2017 | Schneider ............. A61B 17/12 |
| 2018/0184920 | A1* | 7/2018 | Rabinovich ........ A61B 5/02438 |
| 2018/0206746 | A1* | 7/2018 | Narasimhan ......... A61B 5/0225 |
| 2018/0235468 | A1 | 8/2018 | Khachaturian et al. |
| 2019/0150765 | A1 | 5/2019 | Fortin et al. |
| 2019/0365260 | A1* | 12/2019 | Kitagawa ............. A61B 5/6824 |
| 2020/0015689 | A1* | 1/2020 | Allen ................. A61B 5/02241 |
| 2020/0060561 | A1* | 2/2020 | DeBusschere ..... A61B 5/02416 |

OTHER PUBLICATIONS

Bernardi, L., et al., "Noninvasive Assessment of Central Circulatory Pressures by Analysis of Ear Densitographic Changes During the Valsalva Maneuver," American Journal of Cardiology 64:787-792, 1989.

Forfia, P.R., "Blood Pressure Response to the Valsalva Maneuver: A Simple Bedside Test to Determine the Hemodynamic Basis of Pulmonary Hypertension," Journal of the American College of Cardiology—Correspondence 56(16): 1352-1353, 2010.

Galiatsatos, P., et al., A Finger Photoplethysmography Waveform During the Valsalva Maneuver Detects Changes in Left Heart Filling Pressure After Hemodialysis, BMC Nephrology 16:138, 2015, 7 pages.

Galiatsatos, P., "A Noninvasive, Hand-Held Device for Assessing Left Ventricular End-Diastolic Pressure Based on Finger Photoplethysmography and the Valsalva Maneuver," PowerPoint Presentation, Feb. 2, 2013, Johns Hopkins Bayview Medical Center, 21 pages.

Galiatsatos, P., et al., "A Noninvasive, Hand-Held Device for Assessing Left Ventricular End-Diastolic Pressure Based on Finger Photoplethysmography and the Valsalva Maneuver," Journal of the American College of Cardiology vol. 67, Issue 13 Supplement, Apr. 2016, 1-page abstract.

Galiatsatos, P., et al., "Usefulness of a Noninvasive Device to Identify Elevated Left Ventricular Filling Pressure Using Finger Photoplethysmography During a Valsalva Maneuver," American Journal of Cardiology 119(7):1053-1060, Apr. 2017.

Gillard, C., et al., "Operating Characteristics of the Finapress System to Predict Elevated Left Ventricular Filling Pressure," Clinical Cardiology 29:107-111, 2006.

Givertz, M.M., et al., "Noninvasive Determination of Pulmonary Artery Wedge Pressure in Patients With Chronic Heart Failure," American Journal of Cardiology 87:1213-1215, May 2001.

Hébert, J.-L., et al., "Pulse Pressure Response to the Strain of the Valsalva Maneuver in Humans With Preserved Systolic Function," Journal of Applied Physiology 85(3):817-823, 1998.

Marik, P.E., "The Systolic Blood Pressure Variation as an Indicator of Pulmonary Capillary Wedge Pressure in Ventilated Patients," Anaesthesia and Intensive Care 21(4):405-408, Aug. 1993; 1-page abstract.

McIntyre, K.M., et al., "Validation and Clinical Applications of a Non-Invasive Valsalva Response Recorder," Journal of Applied Cardiology 2(2):137-169, 1987.

McIntyre, K.M., et al., "A Noninvasive Method of Predicting Pulmonary-Capillary Wedge Pressure," New England Journal of Medicine 327(24):1715-1720, Dec. 1992.

McIntyre, K.M., et al., "Noninvasive Method of Predicting Pulmonary-Capillary Wedge Pressure," letter to the editor, New England Journal of Medicine 327(19):1423-1424, May 1993.

Remmen, J.J., et al., "Normal Values of Pulmonary Capillary Wedge Pressure and the Blood Pressure Response to the Valsalva Manoeuvre in Healthy Elderly Subjects," Clinical Physiology and Functional Imaging 25(6):318-326, Nov. 2005; 3-page abstract.

Remmen, J.J., et al., "Detection of Elevated Polmonary Capillary Wedge Pressure in Elderly Patients With Various Cardiac Disorders by the Valsalva Manoeuvre," Clinical Science 111:153-162, 2006.

Remmen, J., "Non-Invasive Assessment of Pulmonary Capillary Wedge Pressure in the Elderly by the Valsalva Manoeuvre," Master's Thesis, Radboud University Nijmegen, 169 pages.

Sharma, R.G., et al., "Accuracy and Reproducibility of Noninvasively Determined Left Ventricular End Diastolic Pressure in the Catheterization Laboratory and the Office Setting," Abstract 1014-153, JACC, Poster Session, p. 129A, Mar. 6, 2002, 1-p. abstract.

Sharma, G.V.R.K., et al., "Evaluation of a Noninvasive System for Determining Left Ventricular Filling Pressure," Archives of Internal Medicine 162(18):2084-2088, Oct. 2002.

Sharma, G.V.R.K., et al., "Noninvasive Tracking of Acute Changes in Left Ventricular End-Diastolic Pressure by the Vericor System," Journal of Cardiac Failure, vol. 8, No. 4 Suppl., abstract 327, p. S88, 2002.

Sharma, G.V.R.K., et al., "Suitability of the VeriCor® System, a Non-Invasive Device That Estimates Left Ventricular End-Diastolic Pressure for Screening Patients at High Risk of Developing Heart Failure," HFSA 7th Annual Scientific Meeting, abstract 424, p. S113, 2003.

Sharma, G.V.R.K., et al., "Left Ventricular End-Diastolic Pressure Guided Treatment of Patients Hospitalized for Heart Failure Reduces Rehospitalization Rate," Journal of Cardiac Failure, vol. 15, No. 6S Suppl., abstract 289, p. S88, 2009.

Sharma, G.V.R.K., et al., "Noninvasive Monitoring of Left Ventricular End-Diastolic Pressure Reduces Rehospitalization Rates in Patients Hospitalized for Heart Failure: A Randomized Controlled Trial," Journal of Cardiac Failure 17(9):718-725, 2011.

Silber, H.A., et al., "Finger Photoplethysmography During the Valsalva Maneuver Reflects Left Ventricular Filling Pressure," American Journal of Physiology Heart and Circulatory Physiology 302(10):H2043-H2047, May 2012.

"Vixiar Indicor™: Point of Care, Non-Invasive, Cost Effective, Solution for Assessing Cardiac Filling Pressure," ©2016 Vixiar, <https://vixiar.com/technology/> [retrieved Jul. 2, 2018], 3 pages.

Uehara, H., et al., "A New Method of Predicting Pulmonary Capillary Wedge Pressure: The Arterial Pressure Ratio," Anaesthesia 55:113-117, 2000.

Van Kraaij, D.J.W., et al., "Use of the Valsalva Manoeuvre to Identify Haemodialysis Patients at Risk of Congestive Heart Failure," Nephrology Dialysis Transplantation 13:1518-1523, 1998.

Weilenmann, D., et al., "Noninvasive Evaluation of Pulmonary Capillary Wedge Pressure by BP Response to the Valsalva Maneuver," Chest 122:140-145, 2002.

Xu, H., et al., "Prediction of Pulmonary Arterian Wedge Pressure From Arterial Pressure or Pulse Oximetry Plethysmographic Waveform," Chinese Medical Journal 115(9):1372-1375, 2002.

Zema, M.J., et al., "Left Ventricular Dysfunction—Bedside Valsalva Manoeuvre," British Heart Journal 44:560-569, 1980.

International Search Report and Written Opinion, mailed May 27, 2022, in corresponding International Patent Application No. PCT/US2022/018698, 13 pages.

* cited by examiner

US 12,150,742 B1

HAND-HELD APPARATUS FOR NONINVASIVE MEASUREMENT OF A HEART PERFORMANCE METRIC

CROSS-REFERENCE TO RELATED APPLICATION

This application claims the benefit of U.S. Provisional Application No. 63/160,148, filed Mar. 12, 2021, which is hereby incorporated by reference in its entirety.

TECHNICAL FIELD

This disclosure relates generally to devices for measuring the performance of the heart, and in particular but not exclusively, relates to devices for measuring blood pressure, such as left ventricular filling pressure.

BACKGROUND INFORMATION

Heart failure (HF) is commonly defined as the inability of the heart to maintain an adequate circulation of blood, or the ability only to do so at the expense of increased filling pressures. HF is a grouping of clinical findings, rather than a specific diagnosis or a single disease, and can be considered a symptom of impairment of the pumping action and/or filling of the heart that is caused by an underlying disease. The circulation of blood is quantified by cardiac output, which is dependent on heart rate, contractility, preload, and afterload. Increased preload, driven by increased filling pressure, is one physiological response to increase cardiac output to meet the body's requirements. However, the elevated pressure leads to pulmonary congestion. Additional congestion occurs as fluid "backs up" in the venous system. As the congestion worsens, the resulting symptoms (dyspnea, orthopnea) become debilitating for the patient.

One conventional HF measurement device has been developed for the chronic monitoring of filling pressures, specifically the pulmonary arterial diastolic pressure as an estimate of the left-sided filling pressure. This device has demonstrated that filling pressures typically increase well before other heart failure symptoms become apparent, and studies have demonstrated that filling pressures can be used to effectively guide intervention and optimize therapy to improve outcomes. Unfortunately, this conventional HF measurement device is an invasive, implantable hemodynamic monitor that is restricted for use with only a subset of HF patients. The ability to perform filling pressure measurements non-invasively would broaden the selection criteria to potentially include the chronic monitoring and management of stable individuals with HF.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1A:
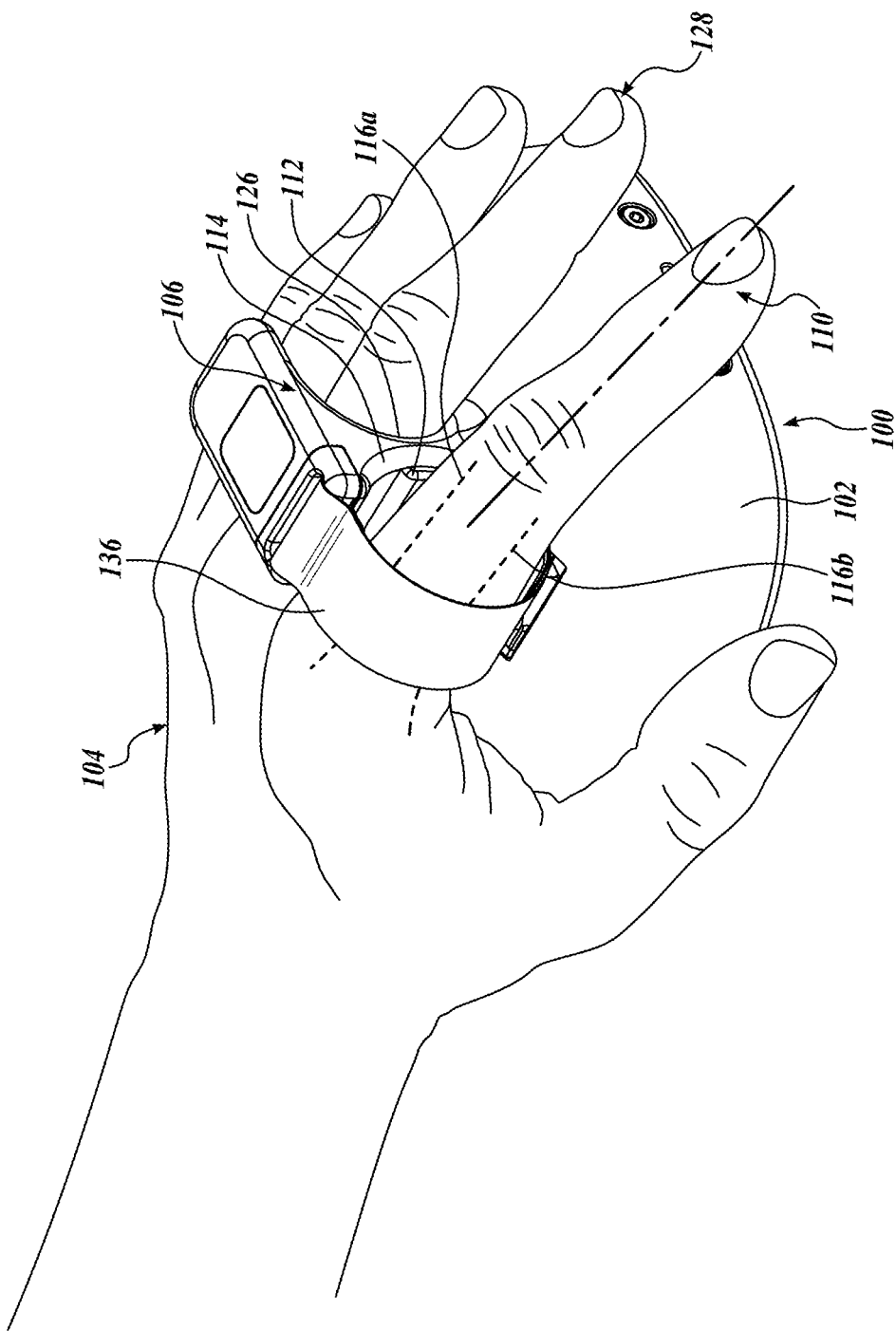
FIG. 1A is a perspective view of an apparatus, in accordance with an embodiment of the present disclosure, shown being held by a hand.

Embodiments of an apparatus, machine-readable storage medium, and method for noninvasively measuring a heart performance metric, such as left ventricular filling pressure, are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

A heart performance measurement apparatus capable of non-invasively measuring a performance metric of the heart, such as left ventricular filling pressure (e.g., left ventricular end diastolic pressure (LVEDP)), is described. While LVEDP will be discussed further herein with respect to certain embodiments of the present disclosure, it will be understood that other measurements, such as pulmonary capillary wedge pressure (PCWP) measurements, are possible and within the scope of the present disclosure. These non-invasive measurements can be performed in an outpatient clinical setting or even at home. The described apparatus provides a less invasive and less expensive alternative to conventional devices, which means it can be deployed more widely and make a significant impact in reducing both the financial cost and quality of life burden of heart failure (HF) in the general public. The heart performance measurement apparatus is capable of monitoring filling pressure, such as through measuring LVEDP and/or PCWP, over time, which can be used to guide patient intervention and improve outcomes (e.g., defined as decreased rate of re-hospitalizations and improved quality of life metrics). The heart performance measurement apparatus may be used for HF screening and diagnosis using filling pressure levels, pre-discharge therapeutic optimization of filling pressure levels, and chronic long-term monitoring at home. The heart performance measurement apparatus provides a reproducible and predictable measurement of the arterial response to allow estimates of the absolute baseline filling pressure value as well as trending changes in the filling pressure over time. In various embodiments, the heart performance measurement apparatus uses tonometry of a digital artery to monitor the pulsatility of the arterial response. Due to the ease of use, high-compliance daily at home use is believed to be achievable.

In various embodiments, the heart performance measurement apparatus measures filling pressure based on arterial blood pressure responses to increased intrathoracic pressure using a forced expiratory effort maneuver (e.g., Valsalva-like maneuver). The Valsalva-like maneuver raises intrathoracic pressure, diminishes venous return to the heart and stroke volume, and increases venous pressure. Arterial-pressure tracings (blood pressure pulsatility) generally show four distinct phases in response to the Valsalva maneuver performed by healthy individuals. In phase 1, the arterial pressure rises as a direct result of the transmission to the periphery of the increased intrathoracic pressure; in phase 2, reductions in systolic, diastolic, and pulse pressures occur as a result of reduced venous return with continuing strain; phase 3 begins with the release of the strain (e.g., cessation of expiratory effort), which results in a sudden drop in arterial pressure; and in phase 4 the arterial pressure overshoots to levels above control, with a widened pulse pressure. Additionally, at expiratory pressures >20 mmHg, the heart rate generally (but not always) increases during phase 2 and then decreases in phase 4. This expected pattern can be measured and analyzed in the user's blood pressure pulsatility signals acquired before, during, and after a forced expiratory effort maneuver.

Figure 1B:
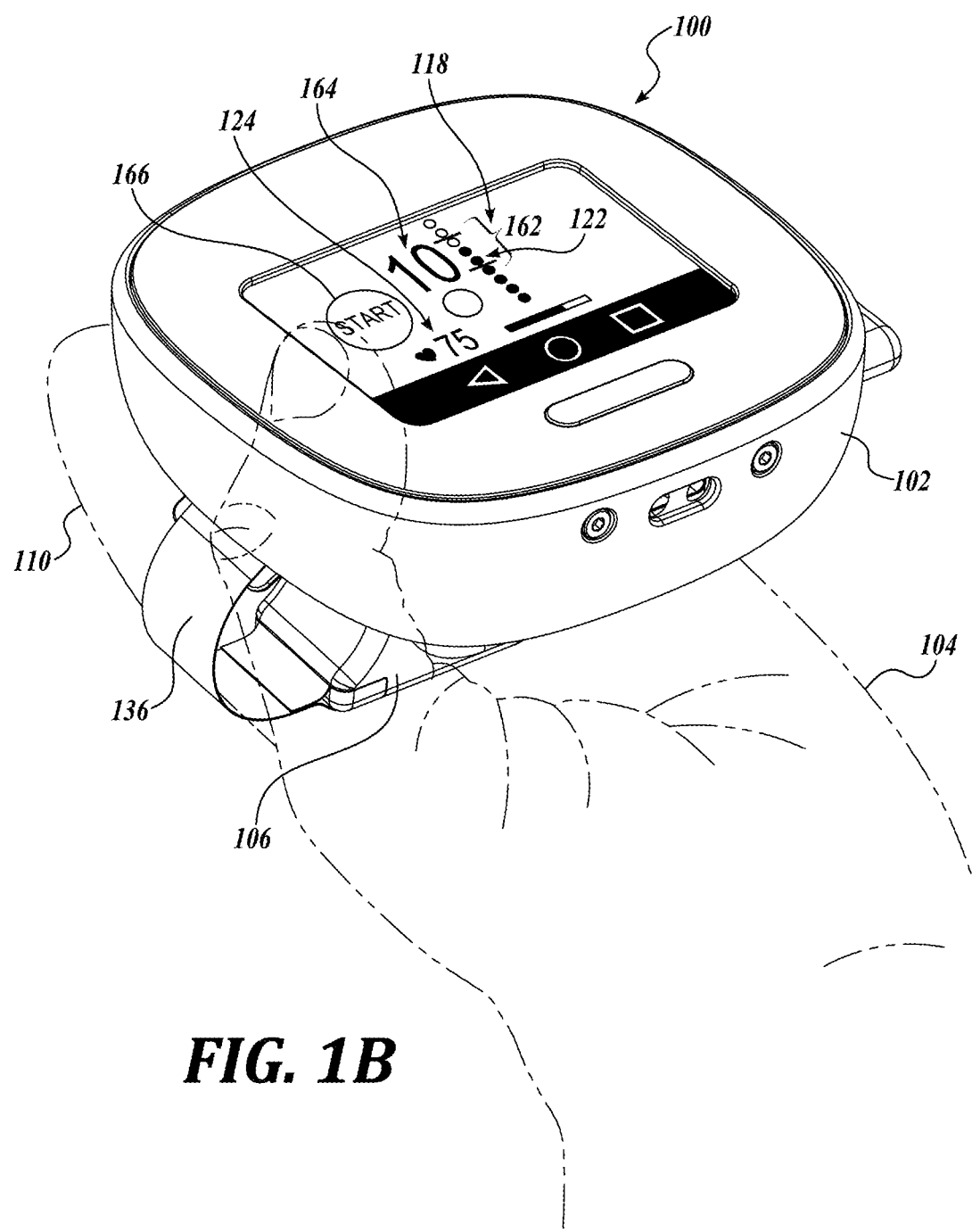
FIG. 1B is another perspective view of the apparatus of FIG. 1A, in accordance with an embodiment of the present disclosure.
Figure 1C:
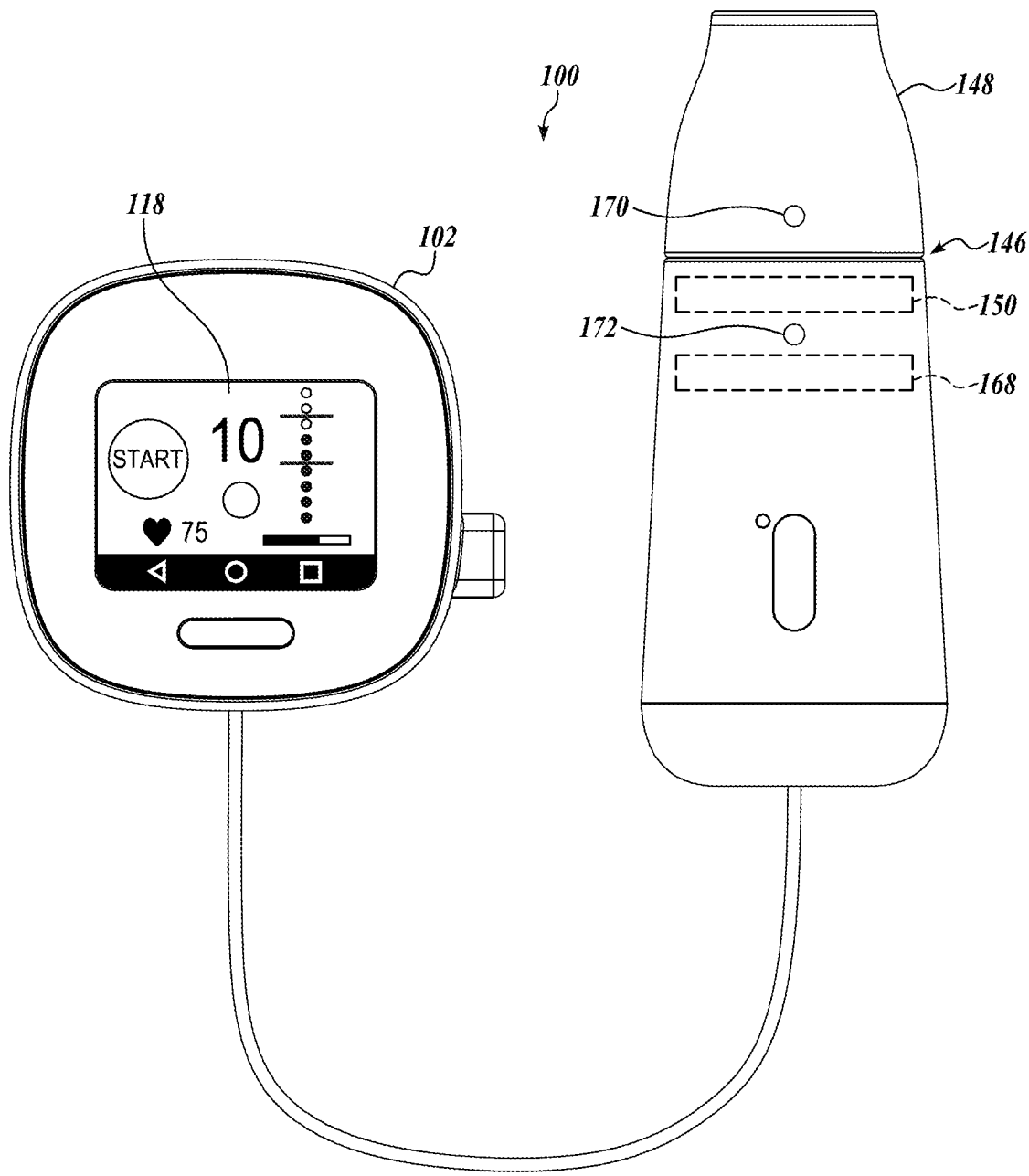
FIG. 1C is a plan view of the apparatus of FIG. 1A, in accordance with an embodiment of the present disclosure.
Figure 1D:
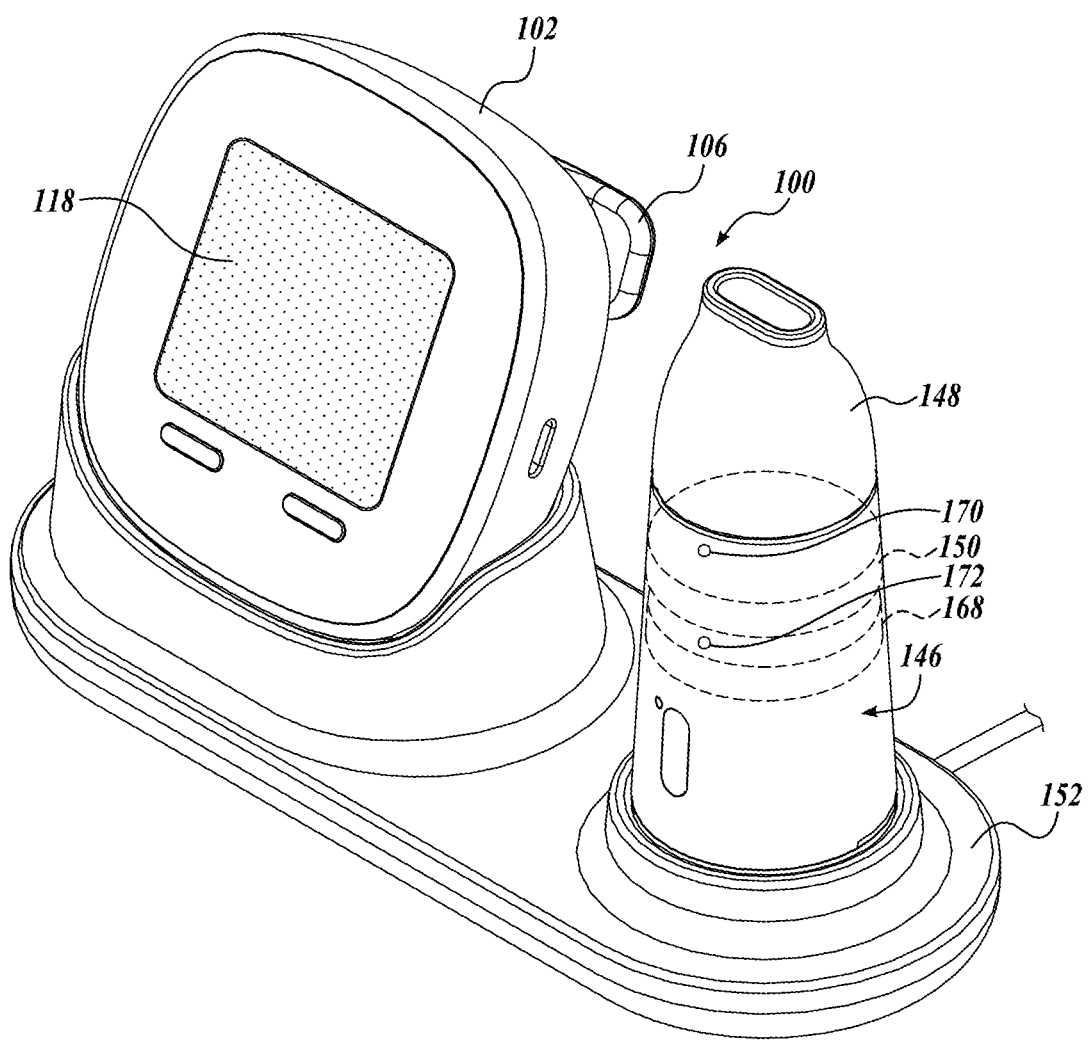
FIG. 1D is a perspective view of the apparatus of FIG. 1A including a docking station, in accordance with an embodiment of the present disclosure.
Figure 1E:
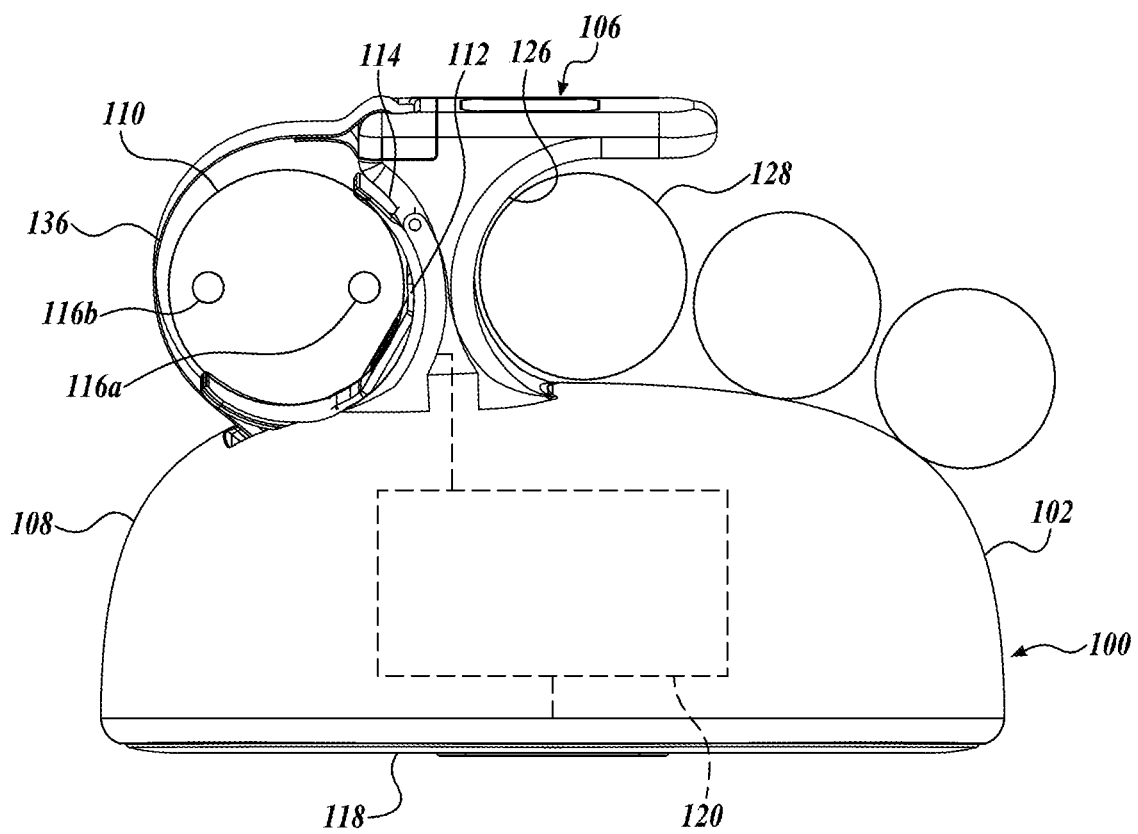
FIG. 1E is a front view of the apparatus of FIG. 1A shown held by a hand, in accordance with an embodiment of the present disclosure.

FIGS. 1A-1E illustrate an apparatus 100, in accordance with an embodiment of the disclosure. FIG. 1A is a perspective view of the apparatus 100, in accordance with an embodiment of the present disclosure. FIG. 1B is another perspective view of the apparatus 100. FIG. 1C is a plan view of the apparatus 100. FIG. 1D is a perspective view of the apparatus 100 including a docking station. FIG. 1E is a front view of the apparatus 100 shown held by a hand 104.

As shown, the apparatus 100 includes a housing 102 shaped to be grasped by a hand 104; a tower 106 protruding from a surface 108 of the housing 102; a tactile sensor 112 disposed on a curved surface 114 of the tower 106; a graphical user interface 118 for orchestrating a test of the performance metric of the heart and displaying results of the test; a controller 120 operatively coupled to the tactile sensor 112 and the graphical user interface 118.

As above, the housing 102 is shaped to be grasped by a hand 104. In an embodiment, the apparatus 100 including the housing 102 is sized and shaped to be held by the hand 104. In an embodiment, the size and general curvature of the housing 102 and weight of the apparatus 100 is suitable to be easily grasped by a hand 104. In this regard, the apparatus 100 including the sensor can be held by a hand 104. In the illustrated embodiment, the housing 102 defines a smooth curved outer surface 108, such as without sharp angles or points.

Movement of the hand 104 and, in particular, a portion of the index finger 110 that contacts the tactile sensor 112 can generate motion-based artefacts in signals generated by the tactile sensor 112. Such motion-based artefacts can make interpreting pulsatility signals more difficult and even impossible to interpret. By shaping the apparatus 100, in general, and the housing 102, which carries the tactile sensor 112, in particular, such that it is suitable to be grasped and held by a hand 104, motion-based artefacts are reduced or eliminated. In this regard, as a hand 104 holding the apparatus 100 moves, an amount that an index finger 110 temporarily presses upon the tactile sensor 112, which generates a corresponding motion-based artefact, is reduced. Accordingly, the apparatus 100 according to the present disclosure is suitable to generate more accurate pulsatility signals than, for example, a device shaped and sized to remain on a desk or tabletop or otherwise configured such that it does not move with a hand 104 contacting the device.

As above, the apparatus 100 includes a tower 106 protruding from a surface 108 of the housing 102. In the illustrated embodiment, the tower 106 is positioned on a portion of the housing 102 such that the tower 106 is configured to conform to an index finger 110 of the hand 104 when grasping the housing 102. As also shown, the tactile sensor 112 is disposed on a curved surface 114 of the tower 106. In this regard, the curved surface 114 of the tower 106 is suitable to conform to a side, such as an ulnar side, of an index finger 110 of a hand 104 grasping the housing 102. In an embodiment, the curved surface 114 is shaped to conform to the size and shape of the side of the index finger 110 such that it makes even contact with and distributes pressure to a portion of the entire side of the index finger 110. Such even contact avoids applying pressure to limited portions of the index finger 110, which could, for example, occlude an ulnar side digital artery 116a and cause discomfort for a user. Not occluding the veins within the index finger 110 ensures there is a return path in the index finger 110 to maintain blood flow during the testing.

In an embodiment, the curved surface 114 is a rigid, solid curved surface 114. In another embodiment, the curved surface 114 comprises a material or structure suitable to conform to a finger in contact with the curved surface 114. In an embodiment, the conformable material or structure includes a fluid bladder housing a gas or incompressible liquid that conforms to fingers of different sizes to apply uniform pressure thereto.

In the illustrated embodiment, such as particularly illustrated in FIG. 1E, the tower 106 defines a second curved surface 126 opposite the curved surface 114. The second curved surface 126 is shaped and positioned to conform to a side of a middle finger 128 of the user, such as when a user grasps or holds the housing 102 with a hand 104. As shown, the second curved surface 126 is shaped and positioned to comfortably align the hand 104 over the housing 102 such that the index finger 110 is correspondingly aligned with the tactile sensor 112 when the hand 104 is grasping or holding the housing 102. Such comfortable alignment of the index finger 110 is suitable to improve a user experience and generate accurate pulsatility signals from the tactile sensor 112.

In the illustrated embodiment, the apparatus 100 is shown to include a strap 136 coupleable to the tower 106. As shown, the strap 136 is coupled to the housing 102 and the tower 106 and is shaped to wrap around the index finger 110. In an embodiment, the strap 136 is positioned and oriented to apply pressure, such as with a clamping force, to the index finger 110 while the housing 102 is grasped by the hand 104. In this regard, the strap 136 is suitable to maintain pressure and/or contact between the index finger 110 and the tactile sensor 112, such as when pulsatility data is being generated. In an embodiment, the strap 136 is releasably coupleable to the tower 106, such that a user can uncouple the strap 136 from the tower 106 to release the index finger 110 more easily.

In one embodiment, a force applied by the strap 136 to index finger 110 is sufficient to reduce transmembrane wall pressure of the digital artery 116a but does not fully occlude the digital artery 116a (e.g., ulnar side digital artery 116a) or the opposing digital artery 116b (e.g., radial side digital artery 116b). Rather, the actuation of strap 136 is controlled to achieve a reduction of transmembrane wall pressure, but not full occlusion or sweeping full occlusion to partial occlusion as is the case with traditional blood pressure meters with bladders or cuffs.

As above, the apparatus 100 includes a tactile sensor 112 disposed in or on a curved surface 114 of the tower 106. In the illustrated embodiment, the tactile sensor 112 conforms to a curvature of the curved surface 114 of the tower 106. The sensor is configured to generate one or more signals for measuring a performance metric of the heart. In an embodiment, the tactile sensor 112 is adapted to measure blood pressure pulsatility in a digital artery 116a of the index finger 110. In a further embodiment, the sensor is adapted to measure blood pressure pulsatility by tonometry and output pulsatility signals indicative of the blood pressure pulsatility.

While a tactile sensor 112 disposed on a curved surface 114 is described as shaped and configured to contact an index finger 110 when the housing 102 is grasped by a hand 104, it will be understood that the tower 106 can be placed on different portions of the housing 102 such that the tactile sensor 112 is positioned to contact another finger, such as a middle finger, ring finger, thumb, etc. when the housing 102 is grasped by the hand 104.

Embodiments of the tactile sensor 112 are not limited to tonometry. Other implementations of the tactile sensor 112 may use other techniques for sensing blood pressure pulsatility (e.g., PPG photoplethysmography (PPG) sensor, oscillometry, auscultation, photoacoustic ultrasound, etc.).

The housing 102 may include other auxiliary sensors. For example, such auxiliary sensors may include an accelerometer disposed in the housing 102 to adjust test readings when the housing 102 is being moved. Auxiliary sensors may also include a temperature sensor disposed on the housing 102 to measure the user's palm or finger temperature and store this data with the blood pressure pulsatility readings. In one embodiment, housing 102 includes a finger or palm heater to warm the hand 104 and/or index finger 110 to a desired temperature. Auxiliary sensors may also include a PPG sensor or a microphone disposed adjacent to the strap 136. The PPG and microphone may be supplemental sources for measuring pulsatility in the index finger 110 or for measuring downstream effects of the applied clamp pressure (such as occlusion or venous blockage resulting in a finger edema and discoloration (turning purple)). Other sensor types (e.g., optical sensors, ballistocardiography sensors, photoacoustic ultrasound, etc.) may also be incorporated.

The apparatus 100 of the present disclosure is suitable to perform noninvasive measurement of a heart performance metric. In an embodiment, the apparatus 100 is adapted to measure a LVEDP. In an embodiment, to measure filling pressure increased intrathoracic pressure using a forced expiratory effort maneuver (e.g., Valsalva-like maneuver) is used. In this regard, in an embodiment, the apparatus 100 includes an expiratory subsystem 146 configured to receive an expiration of a user. In the illustrated embodiment of FIG. 1C, the expiratory subsystem 146 is shown to include a mouthpiece 148 shaped to receive an expiration of a user. In an embodiment, the mouthpiece 148 is shaped to permit a user to place their lips around and blow against resistance. In a clinical setting, mouthpiece 148 may be disposable.

As shown, the expiratory subsystem 146 further includes a pressure sensor 150 coupled to the mouthpiece 148 to measure an air pressure of the expiration. Pressure sensor 150 measures the expiratory effort in the form of air pressure and outputs pressure readings to controller 120. Such a pressure sensor 150 is suitable to monitor the air pressure while generating pulsatility data, such as with the tactile sensor 112. As described further herein, the combination of pulsatility data and air pressure from an expiration of a user is suitable to measure LVEDP.

In the illustrated embodiment of FIG. 1C, the expiratory subsystem 146 is shown physically coupled to the housing 102 by a cable. In another embodiment, the expiratory subsystem 146 is wirelessly coupled to the housing 102, such as through wireless coupling via the controller 120. In an embodiment, the expiratory subsystem 146 and the housing 102 are shaped to removeably couple with a charging dock 152 adapted to provide electrical power to power systems of each of the housing 102 and the expiratory subsystem 146 when coupled to the charging dock 152, as shown in FIG. 1D.

In the illustrated embodiment, the apparatus 100 is shown to include a pinhole leak 170 configured to allow a portion of a user's expiration to pass therethrough. In an embodiment, the pinhole leak 170 is suitable to prevent the user from using their cheek muscles with a closed glottis to generate the expiratory pressure. An uncontrolled Valsalva maneuver (such as including excessive pressure above our 25 to 35 mmHg target) is undesirable due to safety concerns. As also shown, the apparatus 100 also includes a second pressure sensor 168 positioned downstream of the pinhole leak 170 and upstream of a second pinhole leak 172. This allows the apparatus 100 to have single fault detection of failures in either the primary sensor 150, secondary sensor 168, or a blockage of the pinhole leak path by monitoring the pressure ratios between the two sensors 150 and 172. This additional fault protection makes the apparatus 100 more robust and safer to use.

The controller 120 is a functional element that choreographs and controls the operation of the other functional elements. In one embodiment, controller 120 is implemented with hardware logic (e.g., application specific integrated circuit, field programmable gate array, etc.). In yet another embodiment, controller 120 may be implemented as a general-purpose microcontroller 120 that executes software or firmware instructions stored in memory (e.g., non-volatile memory, etc.). Yet alternatively, controller 120 may be implemented in a combination of hardware and software and further may be centralized or distributed across multiple components.

As above, the apparatus 100 includes a graphical user interface 118 operatively coupled to the controller 120 for orchestrating a test of the performance metric of the heart and displaying results of the test. An operator of apparatus 100 interacts with the apparatus 100 via the graphical user interface 118. The graphical user interface 118 may include a variety of hardware and software interfaces, including a screen. In the illustrated embodiment, the graphical user interface 118 is disposed on a portion of the surface 108 of the housing 102 opposite the tower 106. In this regard, as illustrated in FIG. 1B, the graphical user interface 118 is positioned to be easily viewed by a user when holding the housing 102. In particular, as shown, a user can hold the housing 102, thereby placing an index finger 110 in contact with the tactile sensor 112, and simultaneously view the graphical user interface 118 by positioning a palm of their hand 104 upwards toward their face.

In the illustrated embodiment, the graphical user interface 118 includes a screen configured to illustrate or otherwise visually indicate the performance metric of the heart and displaying results of the test. In an embodiment, the graphical user interface 118 includes an expiratory effort meter 122 for displaying when a user is exerting appropriate expiratory effort; and a pulsatility meter 124 for displaying when the blood pressure pulsatility is being sensed by the tactile sensor 112. As discussed further herein, such meters are suitable for conducting tests of the heart metric, such as a cardiac filling pressure, which can include a LVEDP and/or PCWP.

In an embodiment, the apparatuses of the present disclosure include a motor configured to adjust a clamping force of a strap coupleable to the tower. In this regard, attention is directed to FIG. 2 in which an apparatus 200 according to an embodiment of the present disclosure is illustrated. In an embodiment, the apparatus 200 is an example of the apparatus 100 discussed further herein with respect to FIGS. 1A-1E.

As shown, the apparatus 200 includes a housing 202 shaped to be grasped by a hand; a tower 206 protruding from a surface 208 of the housing 202 positioned to conform to an index finger of the hand when grasping the housing 202; a tactile sensor 212 disposed on a curved surface 214 of the tower 206 and adapted to measure blood pressure pulsatility in a digital artery of the index finger and output pulsatility signals indicative of the blood pressure pulsatility; and a controller 220 operatively coupled to the tactile sensor 212 and adapted to generate pulsatility data, based upon the pulsatility signals, from which the performance metric of the heart may be determined In an embodiment, the apparatus 200 further includes a graphical user interface 218 (see for example FIG. 1B) operatively coupled to the controller 220 for orchestrating a test of the performance metric of the heart and displaying results of the test. As discussed further herein, the graphical user interface 218 may be disposed on the surface 208 of the housing 202 opposite the tower 206.

As shown, the apparatus 200 includes a strap 236 coupleable to the tower 206. In the illustrated embodiment, the strap 236 is positioned and oriented to apply pressure to the index finger while the housing 202 is grasped by the hand. As also shown, in partial cutaway, the apparatus 200 further includes a motor 238 operatively coupled to the controller 220 and disposed within the housing 202. As above, the strap 236 is coupleable to the tower 206 and, in this regard, is configured to tighten the strap 236, such as through operation of the motor 238. Such operation of the motor 238 can include rotation of the shaft 260 about which a portion of the strap 236 is wrapped to tighten or loosen the clamping force of the strap 236 on the index finger.

While a motor 238 coupled to a strap 236 is illustrated, it will be understood that other structures and mechanisms for applying pressure to a finger, such as a linear clamp or an air bladder, are possible and within the scope of the present disclosure.

In an embodiment, the controller 220 includes logic that, when executed by the controller 220, causes the apparatus 200 to perform operations including clamping the index finger with the strap 236 to a sufficient pressure to measure the blood pressure pulsatility in the digital artery while not fully occluding the digital artery or an opposing digital artery of the finger. As discussed further herein, in an embodiment, the controller 220 includes logic suitable to optimize or adjust a strap 236 tightness or clamping force to improve pulsatility data.

Figure 3:
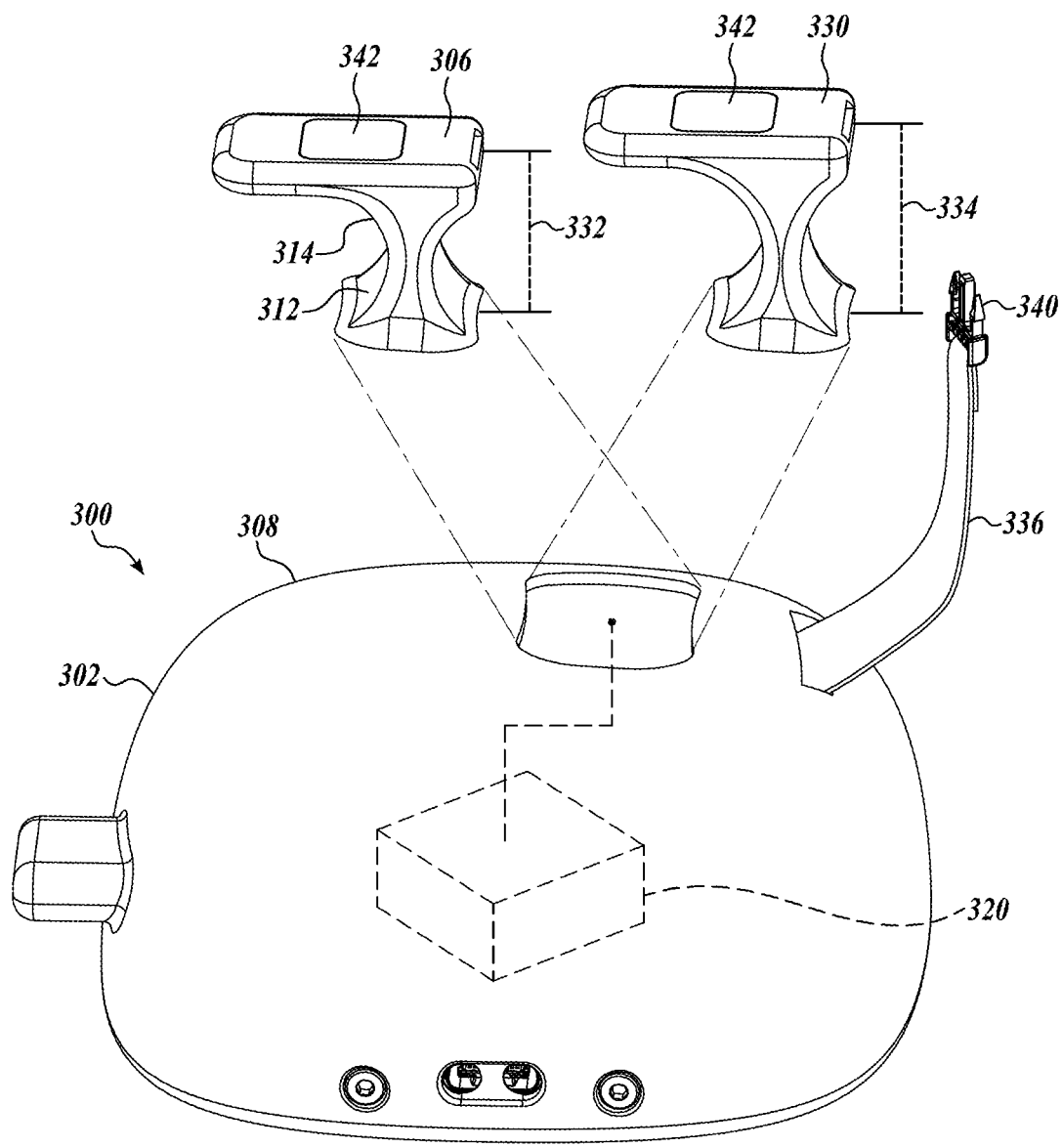
FIG. 3 is a perspective view of an apparatus showing interchangeable towers, in accordance with an embodiment of the present disclosure.

In an embodiment, the apparatuses of the present disclosure include two or more towers coupleable to the housing, such as two or more towers having different heights or sizes suitable for use with fingers of different sizes. In this regard, attention is directed to FIG. 3, where an apparatus 300 according to an embodiment of the present disclosure is illustrated. FIG. 3 is a perspective view of the apparatus 300 showing interchangeable towers 306 and 330, in accordance with an embodiment of the present disclosure.

Figure 2:
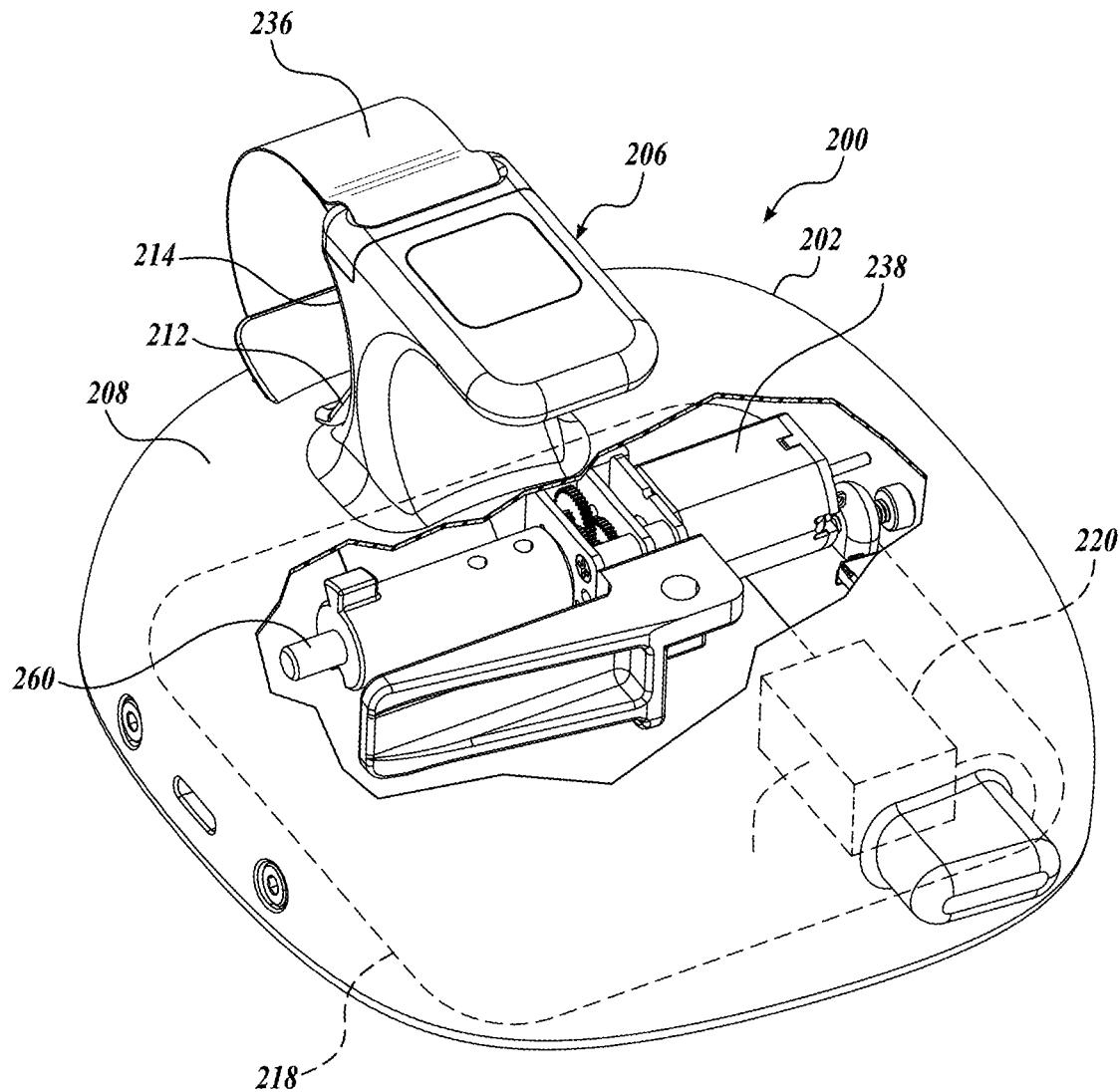
FIG. 2 is a perspective view of an apparatus, in accordance with an embodiment of the present disclosure, showing a partial cutaway.

In an embodiment, the apparatus 300 is an example of the apparatus 100 discussed further herein with respect to FIGS. 1A-1E and/or apparatus 200 discussed further herein with respect to FIG. 2.

As shown, the apparatus 300 includes a housing 302 shaped to be grasped by a hand; a tower 306 protruding from a surface 308 of the housing 302 positioned to conform to an index finger of the hand when grasping the housing 302; a tactile sensor 312 disposed on a curved surface 314 of the tower 306 and adapted to measure blood pressure pulsatility in a digital artery of the index finger and output pulsatility signals indicative of the blood pressure pulsatility; and a controller 320 operatively coupled to the tactile sensor 312 and adapted to generate pulsatility data, based upon the pulsatility signals, from which the performance metric of the heart may be determined.

In an embodiment, the apparatus 300 further includes a graphical user interface (see for example FIG. 1B) operatively coupled to the controller 320 for orchestrating a test of the performance metric of the heart and displaying results of the test. As discussed further herein, the graphical user interface may be disposed on the surface 308 of the housing 302 opposite the tower 306.

As shown, the apparatus 300 includes two towers 306 and 330 coupleable to the housing 302. In this regard, the tower 306 is a first tower 306 selectively coupleable to the housing 302, wherein the apparatus 300 further comprises a second tower 330 selectively coupleable to the housing 302 having a height 334 different from a height 332 of the first tower 306. In this regard, the second tower 330 is shaped to conform to a second index finger of a second hand when grasping the housing 302, the second tower 330 having a different size than the index finger. Coupling of the first tower 306 and the second tower 330 to the housing 302 can occur through any cooperative coupling structures or mechanisms. In an embodiment, such coupling structures include one or more magnets disposed within the first tower 306 and second tower 330 configured to cooperatively couple to corresponding magnet(s) disposed in or on the housing 302.

In embodiment, the first tower 306 and second tower 330 are configured to receive electrical power from the housing 302 when coupled thereto. In an embodiment, the housing 302 includes one or more conductive elements, such as one or more pogo pins, for transferring electrical power from the housing 302 to the first tower 306 and/or the second tower 330 when coupled to the housing 302 to provide power to, for example, the tactile sensor 312. Alternatively, a signal generated by the tactile sensor 312 can be transferred through an optical or magnetic connection between the tactile sensor and the controller 320 disposed within the housing 302.

In the illustrated embodiment, the strap 336 is shown to include a buckle 340 configured to couple to a corresponding structure in a top of the first tower 306 and the second tower 330. As also shown, the first tower 306 and the second tower 330 include a release button 342 configured to release the strap 336 from the first tower 306 or second tower 330 when depressed or otherwise actuated.

Figure 4A:
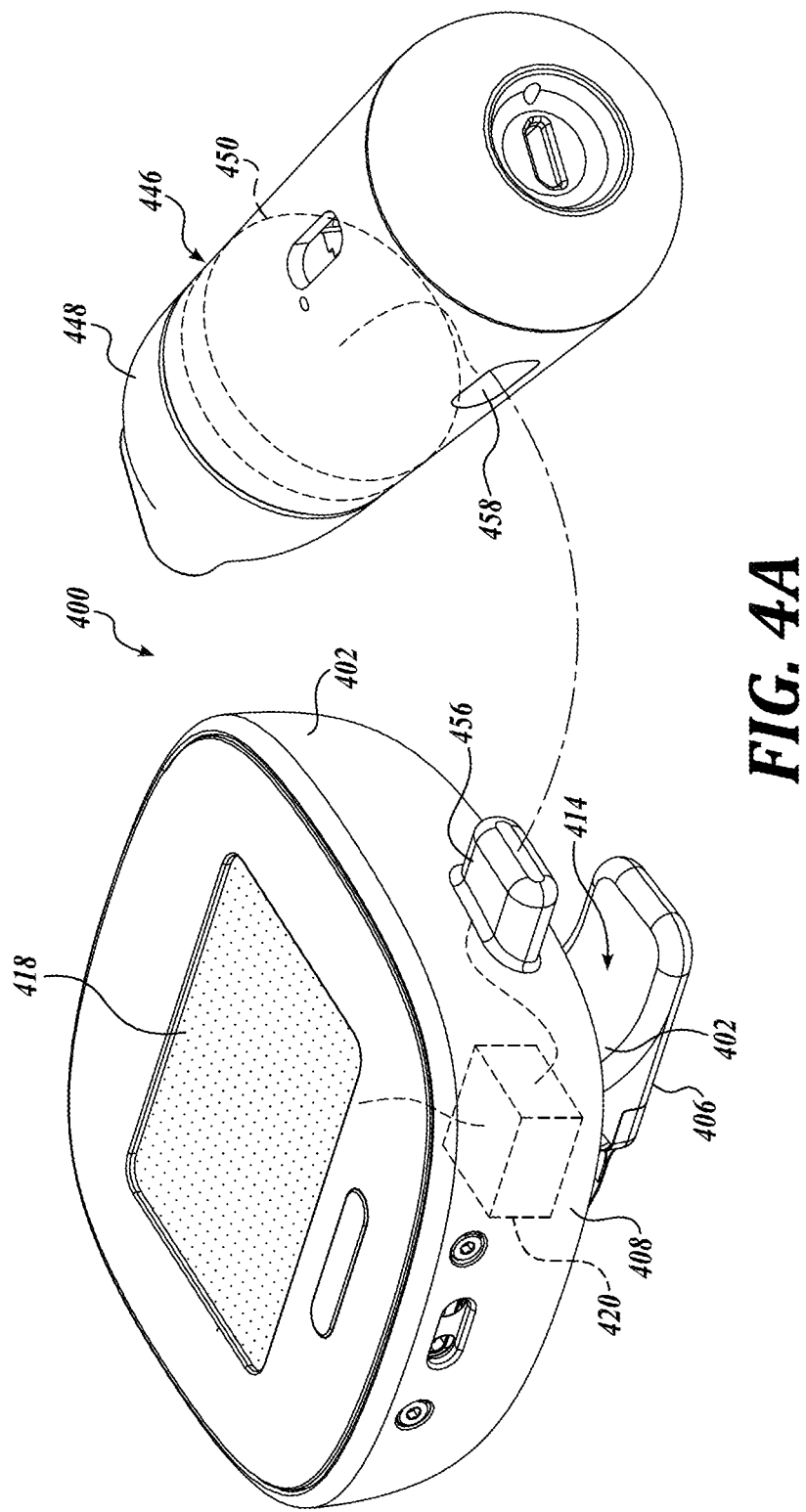
FIG. 4A is a perspective view of an apparatus, accordance with an embodiment of the present disclosure.
Figure 4B:
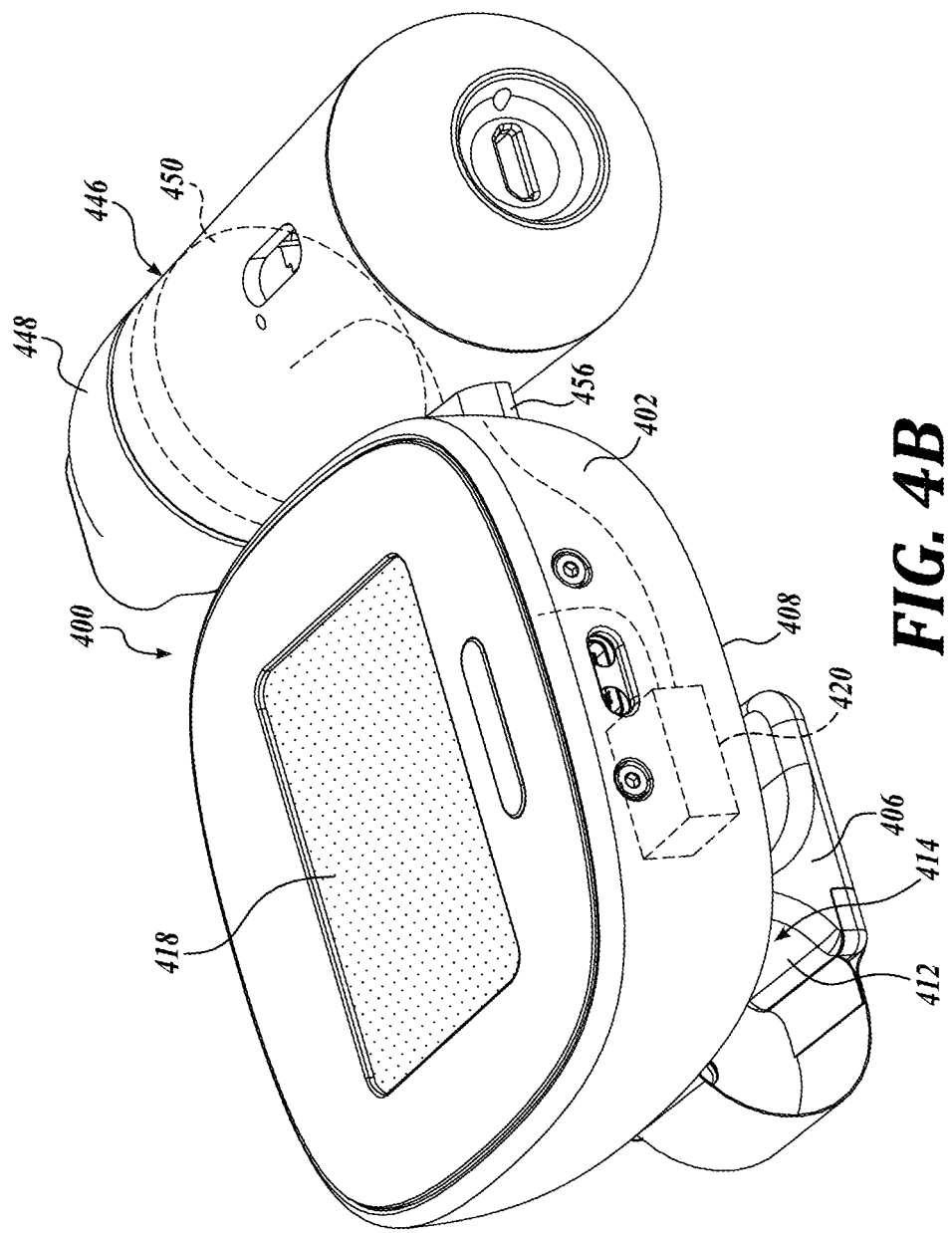
FIG. 4B is another perspective view of the apparatus of FIG. 4A, in accordance with an embodiment of the present disclosure.
Figure 4C:
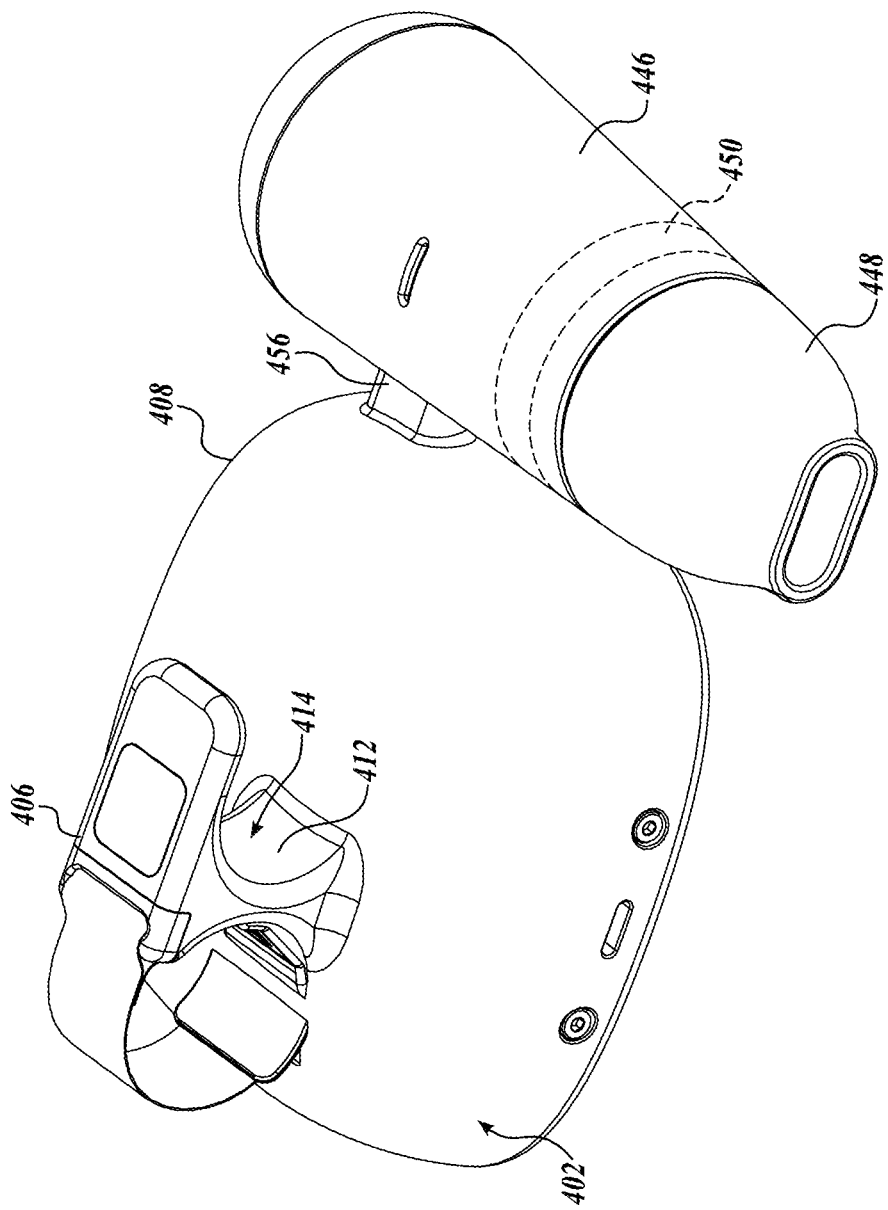
FIG. 4C is another perspective view of the apparatus of FIG. 4A, in accordance with an embodiment of the present disclosure.

In an embodiment, the expiratory subsystems of the apparatuses described herein are removably coupleable to the housings of the apparatuses. In this regard, attention is directed to FIGS. 4A-4C in which an apparatus 400, according to an embodiment of the present disclosure, is illustrated. FIG. 4A is a perspective view of the apparatus 400. FIG. 4B is another perspective view of the apparatus 400. FIG. 4C is another perspective view of the apparatus 400. In an embodiment, the apparatus 400 is an example of the apparatuses 100, 200, and/or 300 discussed further herein with respect to FIGS. 1A-1E, 2, and 3, respectively.

As shown, the apparatus 400 includes a housing 402 shaped to be grasped by a hand; a tower 406 protruding from a surface 408 of the housing 402 positioned to conform to an index finger of the hand when grasping the housing 402; a tactile sensor 412 disposed on a curved surface 414 of the tower 406 and adapted to measure blood pressure pulsatility in a digital artery of the index finger and output pulsatility signals indicative of the blood pressure pulsatility; a graphical user interface 418 for orchestrating a test of the performance metric of the heart and displaying results of the test, wherein the graphical user interface 418 is disposed on the surface 408 of the housing 402 opposite the tower 406; and a controller 420 operatively coupled to the tactile sensor 412 and the graphical user interface 418 and adapted to generate pulsatility data, based upon the pulsatility signals, from which the performance metric of the heart may be determined.

In the illustrated embodiment, the apparatus 400 further includes an expiratory subsystem 446 operatively coupled to the controller 420, the expiratory subsystem 446 comprising a mouthpiece 448 shaped to receive an expiration of a user; and a pressure sensor 450 coupled to the mouthpiece 448 to measure an air pressure of the expiration, wherein the controller 420 is coupled to the pressure sensor 450 and adapted to monitor the air pressure while generating the pulsatility data. As discussed further herein, in this regard, the apparatus 400 is adapted to measure a LVEDP. In the illustrated embodiment, the expiratory subsystem 446 is removably coupleable to the housing 402.

As shown, the expiratory subsystem 446 can be coupled and uncoupled from the housing 402, such as through coupling of the tab 456 of the housing 402 into the slot 458 of the expiratory subsystem 446. In an embodiment, the tab 456 and slot 458 are configured to exchange signals between the expiratory subsystem 446, such as generated with the pressure sensor 450, and the controller 420. While a tab 456 and slot 458 are shown it will be understood that other cooperative coupling structures are possible and within the scope of the present disclosure. It will be further understood that signals can be exchanged between the expiratory subsystem 446 and the controller 420 in a wireless, as well as a wired, configuration.

Figure 5A:
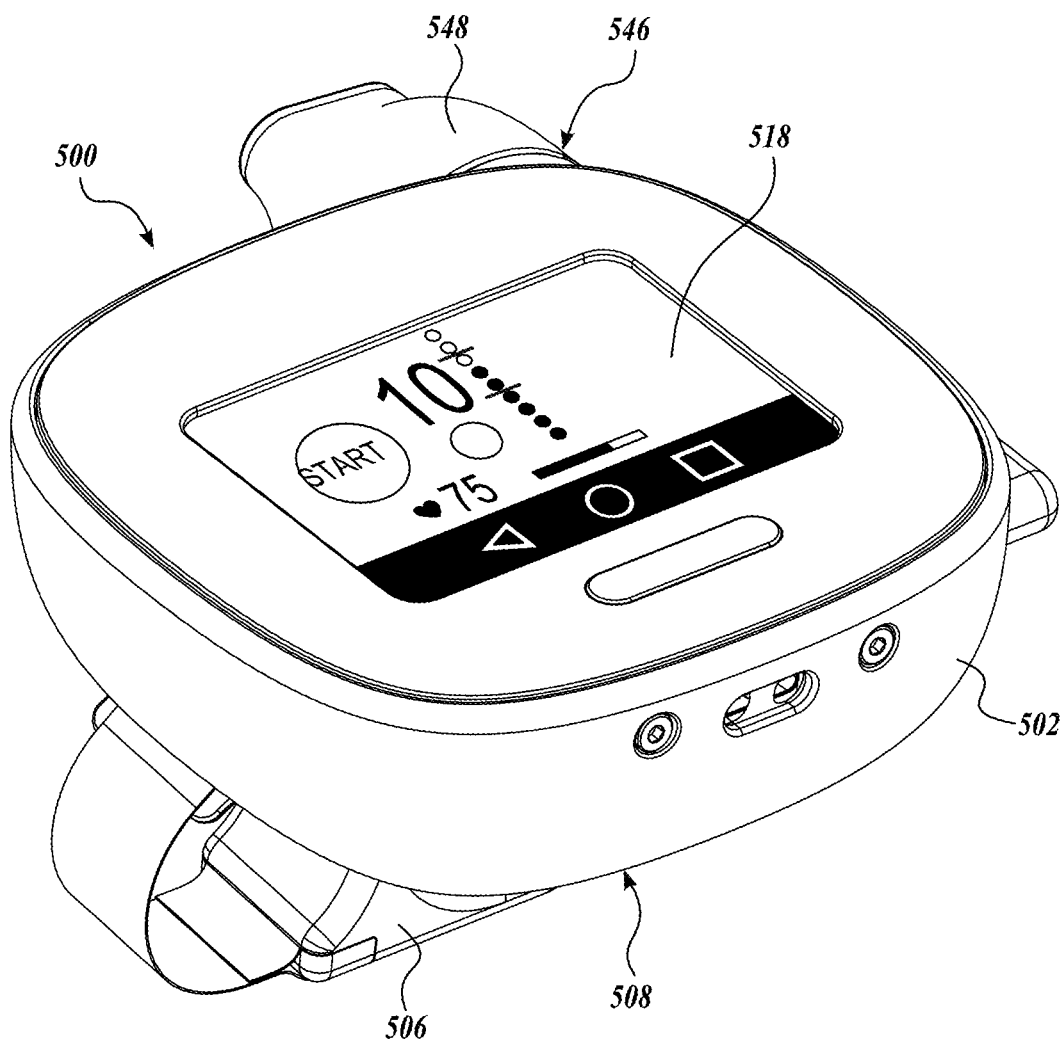
FIG. 5A is a perspective view of an apparatus, accordance with an embodiment of the present disclosure.
Figure 5B:
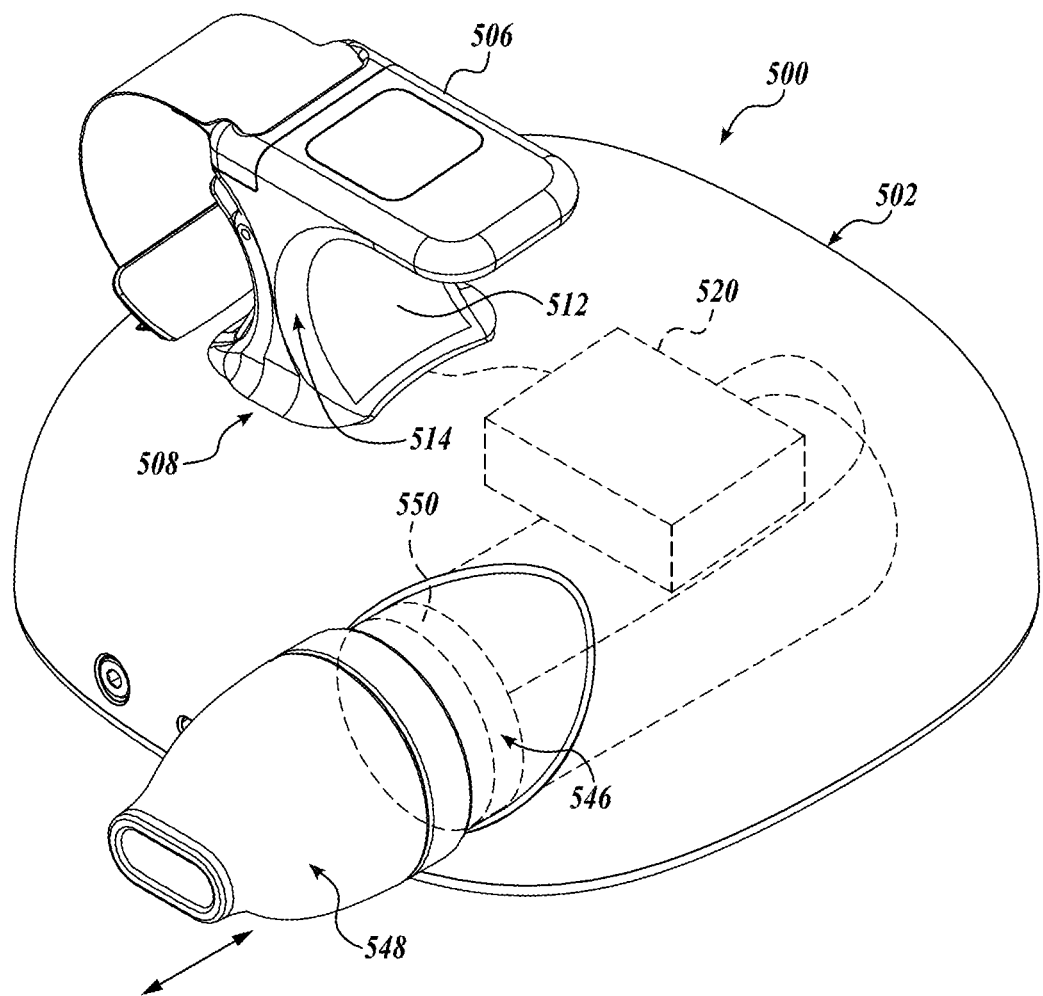
FIG. 5B is another perspective view of the apparatus of FIG. 5A, in accordance with an embodiment of the present disclosure.
Figure 6A:
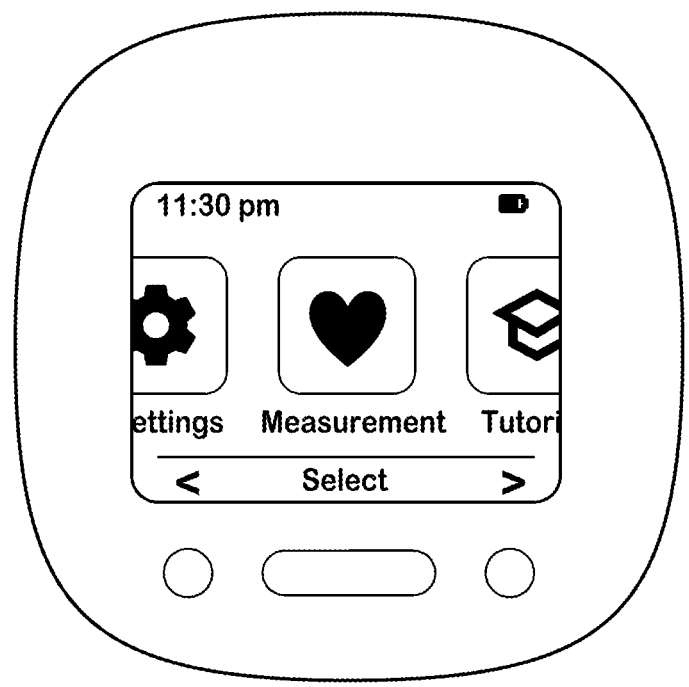
FIGS. 6A-6H illustrate images displayed by a graphical user interface of an apparatus, in accordance with an embodiment of the present disclosure.
Figure 6B:
Figure 6C:
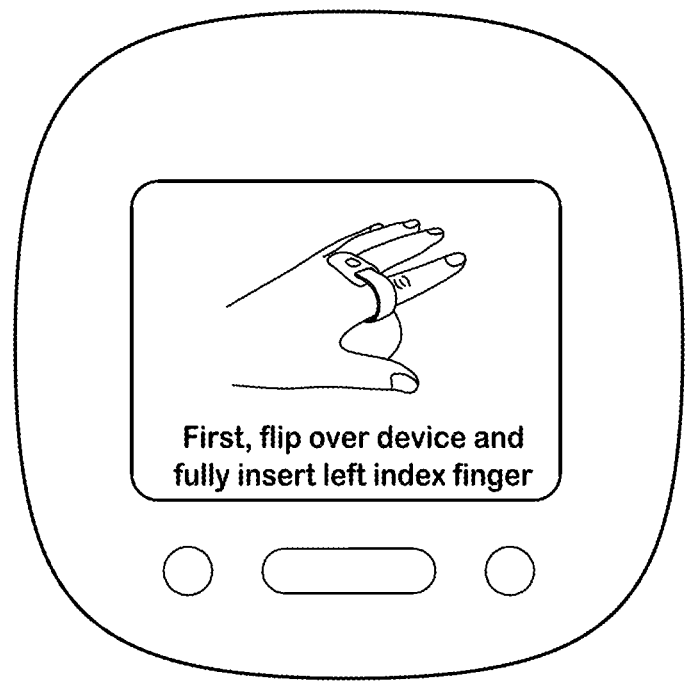
Figure 6D:
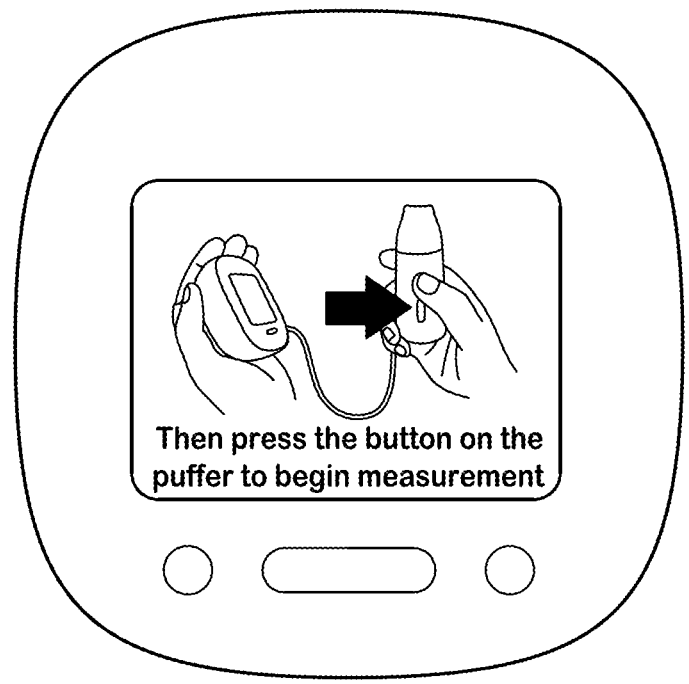
Figure 6E:
Figure 6F:
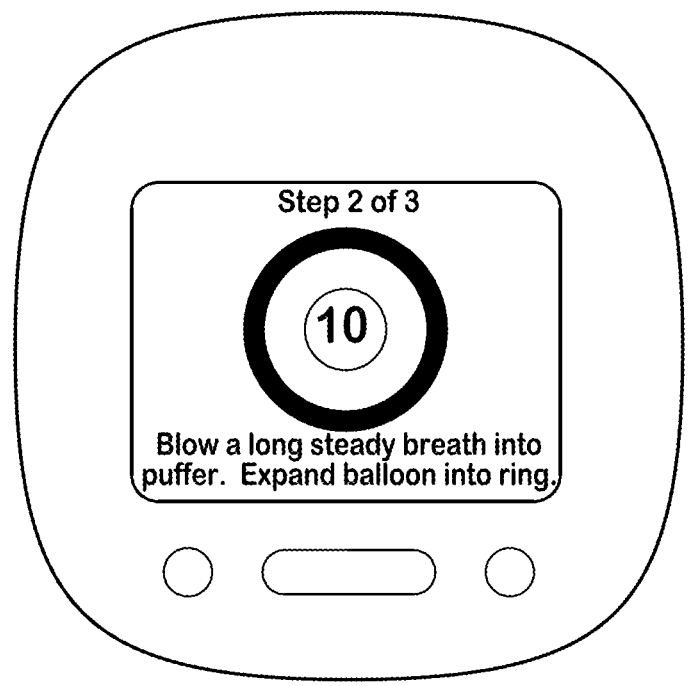
Figure 6G:
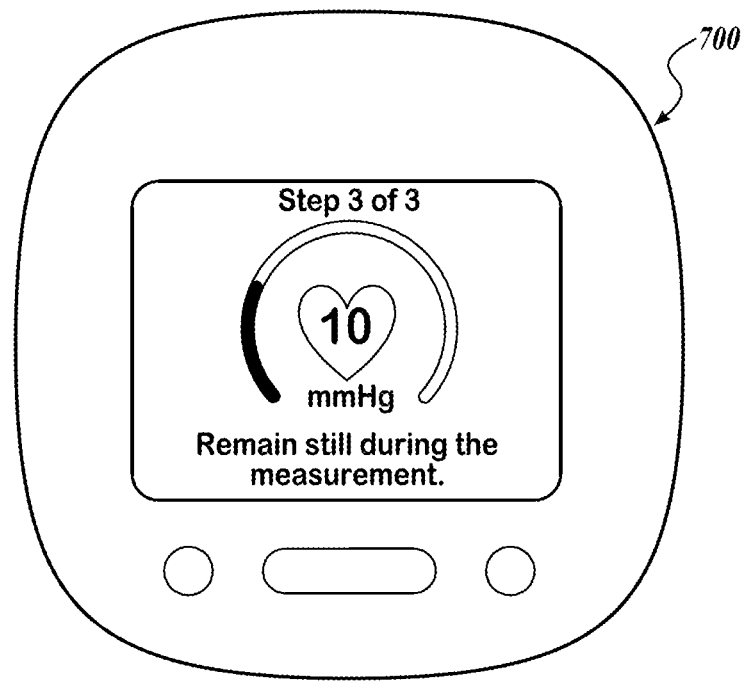
Figure 6H:
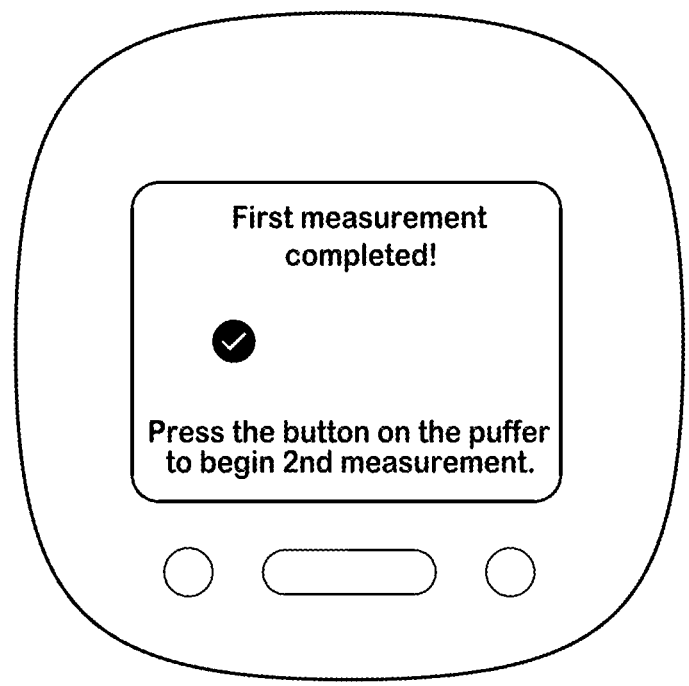

In an embodiment, the apparatuses of the present disclosure include an expiratory subsystem disposed within and/or integrated with a housing of the apparatuses. In this regard, attention is directed to FIGS. 5A and 5B in which an apparatus 500, according to an embodiment of the present disclosure, is illustrated. FIG. 5A is a perspective view of the apparatus 500. FIG. 5B is another perspective view of the apparatus 500. In an embodiment, the apparatus 500 is an example of the apparatuses 100, 200, and/or 300 discussed further herein with respect to FIGS. 1A-1E, 2, and 3.

As shown, the apparatus 500 includes a housing 502 shaped to be grasped by a hand; a tower 506 protruding from a surface 508 of the housing 502 positioned to conform to an index finger of the hand when grasping the housing 502; a tactile sensor 512 disposed on a curved surface 514 of the tower 506 and adapted to measure blood pressure pulsatility in a digital artery of the index finger and output pulsatility signals indicative of the blood pressure pulsatility; a graphical user interface 518 for orchestrating a test of the performance metric of the heart and displaying results of the test, wherein the graphical user interface 518 is disposed on the surface 508 of the housing 502 opposite the tower 506; and a controller 520 operatively coupled to the tactile sensor 512 and the graphical user interface 518 and adapted to generate pulsatility data, based upon the pulsatility signals, from which the performance metric of the heart may be determined.

In the illustrated embodiment, the apparatus 500 further includes an expiratory subsystem 546. As shown, the expiratory subsystem 546 includes a mouthpiece 548 shaped to receive an expiration of a user; and a pressure sensor 550 coupled to the mouthpiece 548 to measure an air pressure of the expiration, wherein the controller 520 is coupled to the pressure sensor 550 and adapted to monitor the air pressure while generating the pulsatility data. As also shown, the expiratory subsystem 546 including the pressure sensor 550 is integrated within the housing 502. The mouthpiece 548 is shown extending from a portion of the housing 502 shaped to receive the user's expiration.

In an embodiment, the expiratory subsystem 546 is removably coupleable to the housing 502 such that a user can remove the expiratory subsystem 546 from the housing 502, such as during performance of a test of a heart performance metric. In this regard, the user can grasp the housing 502 with a first hand such as to view a graphical user interface and place a finger in contact with the tactile sensor 512 and breathe into the expiratory subsystem 546 held in a second hand. In an embodiment, the housing 502 defines a stylus-like storage pocket, such as configured to hold the expiratory subsystem 546 within the housing 502 by friction. Such a stylus-like storage pocket can be suitable to reduce the likelihood of misplacing the expiratory subsystem 546. In an embodiment the housing 502 is configured to supply electrical power to the expiratory subsystem 546 when docked within the housing 502. In an embodiment, the housing 502 is configured to perform wireless pairing with the expiratory subsystem 546 when docked within the housing 502.

Figure 7:
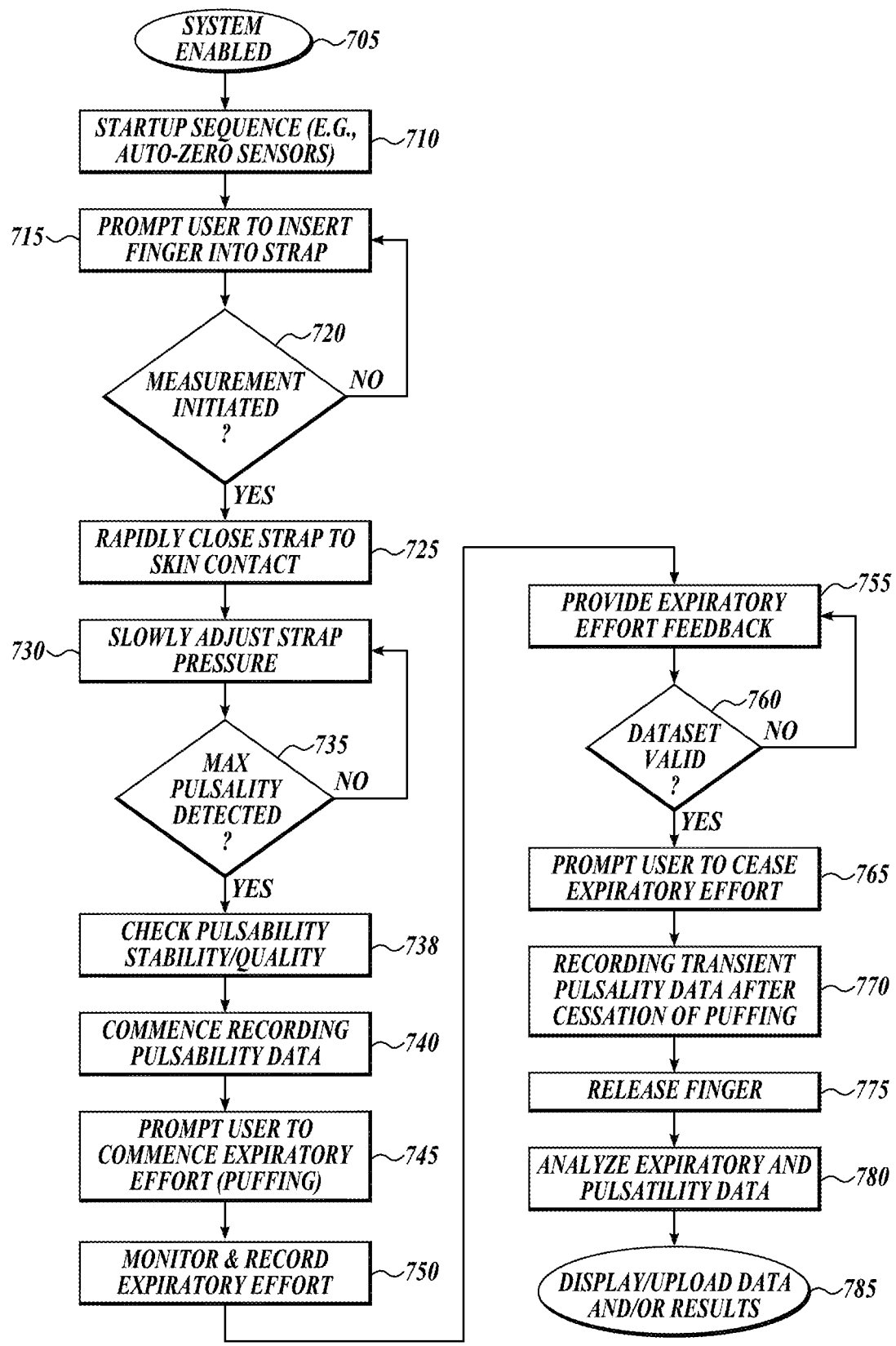
FIG. 7 is a flow chart illustrating operation of a heart performance measurement apparatus, in accordance with an embodiment of the disclosure.

FIG. 7 is a flow chart 700 illustrating operation of heart performance measurement apparatus, such as apparatuses 100, 200, 300, 400, and 500, in accordance with an embodiment of the disclosure. The order in which some or all of the process blocks appear in process 700 should not be deemed limiting. Rather, one of ordinary skill in the art having the benefit of the present disclosure will understand that some of the process blocks may be executed in a variety of orders not illustrated, or even in parallel.

Flow chart 700 will be discussed further herein with respect to apparatus 100 of FIGS. 1A-1E, but is also applicable to apparatuses 200, 300, 400, and 500, discussed elsewhere herein.

In a process block 705, apparatus 100 is enabled. Enabling apparatus 100 may be achieved by pressing a software button on the graphical user interface 118. Enabling apparatus 100 causes apparatus 100 to execute a self-test or startup sequence that auto-zeros various sensors including sensor elements in the tactile sensor 112, motor, pressure sensor 150, etc. (process block 710). The self-test is performed before the user places the index finger on the tactile sensor 112 and into the strap 136.

In a process block 715, the user is prompted by the graphical user interface 118 to insert their finger onto the tactile sensor 112 and into the strap 136. FIGS. 6A-6H illustrate images displayed by the interface 118, in accordance with an embodiment of the present disclosure, such as described further herein with respect to FIG. 7. The prompt may be a message displayed on a screen integrated into the housing 102, an audible prompt, or otherwise. Once the user has inserted their finger into the strap 136 and grasped housing 102, a measurement may be user initiated (decision block 720) via a soft button displayed on the graphical user interface 118. The user's grips need not be firm, but rather in some embodiments, may be a light grip sufficient for the hand to generally conform to the shape of housing 102.

Upon initiation of a heart performance test, controller 120 directs motor, such as motor 238 of FIG. 2, to rapidly close the strap 136 until light skin contact between index finger and the tactile sensor 112 is registered (process block 725). Once light skin contact is registered, the controller 120 reduces the adjustment speed of the motor to a slower speed setting (process block 730) during which the appropriate clamping force is determined for tonometery. In an embodiment, the appropriate clamping force is a force that unloads the arterial walls of a digital artery. By applying a clamping pressure that generates an external pressure around the artery that roughly matches the internal pressure, the pressure across the arterial wall is reduced to near zero. This greatly reduces the non-linear behavior of the arterial wall, which is very similar to applanation tonometry, but without, for example, flattening the artery by compressing it against a rigid back surface.

This appropriate or optimal clamping force is determined by slowly increasing the clamping force while monitoring the amplitude of the blood pressure pulsatility signals sensed from the digital artery. As the clamping force is increased, the blood pressure pulsatility signals should increase up to a maximum, then begin to decrease. Once the amplitude begins to decrease, the controller 120 determines that maximum pulsatility has been detected (decision block 735) and backs off the motor to the position associated with the detected maximum pulsatility. Once the strap 136 has been positioned for maximum pulsatility, the strap 136 maintains a constant clamping force during the filling pressure testing. The ramping range may be optimized or refined on a per user basis to reduce measurement time. Additionally, a stability check and/or pulsatility quality check may be performed at the determined set point for maximum pulsatility by observing pulses for a finite period of time, such as 2-10 seconds (process block 738). In an embodiment, monitoring strap 136 pressure and pulsatility measurements can include monitoring the pulse amplitude and the waveform shape to inform the clamping pressure.

With the strap 136 adjusted to the set point associated with the determined maximum pulsatility and pulsatility stability/quality determined, controller 120 commences recording blood pressure pulsatility data (process block 740) from tactile sensor 112 into memory. In other embodiments, the pulsatility data is also recorded during the stability check to obtain a baseline reference of the blood pressure pulsatility prior to commencing the expiratory maneuver. After recording has commenced, the user is prompted to commence expiratory effort (process block 745). Expiratory effort includes the user puffing or blowing into the mouthpiece 148. The user's expiratory effort is monitored and recorded by controller 120 using pressure sensor 150 (process block 750). The effort level, rise time, duration, and stability may all be monitored/recorded. In a process block 755, the user is provided with real-time feedback for guiding their expiratory effort into a threshold effort range and holding it there for a threshold period of time (e.g., 10 seconds) needed for the heart performance test (e.g., LVEDP test). In one embodiment, an expiratory effort meter 122 is displayed to the user via graphical user interface 118. The graphical user interface 118 output on a display panel integrated into housing 102.

As above, FIG. 1B shows apparatus 100 to include a graphical user interface 118 displaying an expiratory effort meter 122 and a pulsatility meter 124. As illustrated, graphical user interface 118 includes an expiratory effort meter 122 including a threshold effort range 162. The user's expiratory effort is measured based upon air pressure. Graphical user interface 118 also includes a puffing timer 164 that counts down while the user's expiratory effort remains in threshold effort range 162. A soft start/stop button 166 is also provided to commence or terminate a heart performance test. User interface also includes a pulsatility meter 124 that displays a real-time indication of the quality of the blood pulsatility signals received from tactile sensor 112, and in the illustrated embodiment also displays heart rate. Pulsatility meter 124 provides the user with a visual confirmation that their index finger is correctly positioned in the strap 136 and on the tactile sensor 112.

Returning to process 700 illustrated in FIG. 7, once the requisite amount of data has been captured with the user's expiratory effort residing in a threshold effort range 162 (decision block 760), the user is prompted to cease expiratory effort (process block 765). The controller 120 continues to record the blood pressure pulsatility data even after the user ceases expiratory effort (process block 770). For example, the controller 120 may continue to record data for 20 seconds post puffing as the transient pulsatility data is a relevant data for determining the filling pressure. Once the post puffing transient pulsatility data has been recorded, the index finger is released (process block 775) and the expiratory and pulsatility data analyzed by controller 120 (process block 780). The data may be analyzed for deviations from expected signal waveforms for a healthy heart, similarities to characteristic traits, changes or deviations over time from a baseline measurement or pattern, etc. Particular shape characteristics may further be analyzed (e.g., dichrotic notch, frequency content, etc.). In one embodiment, machine learning (ML) may be applied to analyze the waveforms and estimate the filling pressure or other cardiac features. Furthermore, when analyzing the pulsatility data, data recorded from auxiliary sensors may also be analyzed to supplement, augment, replace, or validate the pulsatility data.

Finally, in a process block 785, the pulsatility data, expiratory data, and/or analysis results may be displayed to the user, saved locally for future reference, or uploaded to a cloud-based service. In one embodiment where the user is a patient under the supervision of a doctor or practitioner, the results may be automatically reported to the doctor/practitioner. Although process 700 illustrates a technique for measuring a filling pressure such as LVEDP, other heart performance metrics may also be measured/monitored with apparatus 100. Such metrics may include vascular volume status, heart rate, arrhythmia, systolic and diastolic blood pressure, overnight respiratory activity, variations in cardiac output with respiratory cycles, etc.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An apparatus for measuring a performance metric of a heart, comprising:
    a housing shaped to be grasped by a hand;
    a tower protruding from a surface of the housing positioned to conform to a finger of the hand when grasping the housing;
    a tactile sensor disposed on a curved surface of the tower and adapted to measure blood pressure pulsatility in a digital artery of the finger and output pulsatility signals indicative of the blood pressure pulsatility;
    a graphical user interface for orchestrating a test of the performance metric of the heart and displaying results of the test; and
    a controller operatively coupled to the tactile sensor and the graphical user interface and adapted to generate pulsatility data, based upon the pulsatility signals, from which the performance metric of the heart may be determined.

2. The apparatus of claim 1, wherein the graphical user interface is disposed on the surface of the housing opposite the tower.

3. The apparatus of claim 1, wherein the housing is sized and shaped to be held by the hand.

4. The apparatus of claim 3, wherein the graphical user interface is positioned to be viewed by the user when the apparatus is held by the hand of the user.

5. The apparatus of claim 1, wherein a second curved surface of the tower opposite the curved surface is shaped to conform to a side of a second finger of the hand.

6. The apparatus of claim 1, wherein the tower is a first tower selectively coupleable to the housing, wherein the apparatus further comprises a second tower selectively coupleable to the housing having a height different from a height of the first tower.

7. The apparatus of claim 6, wherein the second tower is shaped to conform to a finger of a second hand when grasping the housing, the second tower having a different size than the finger.

8. The apparatus of claim 1, further comprising a strap coupleable to the tower, wherein the strap is positioned and oriented to apply pressure to the finger while the housing is grasped by the hand.

9. The apparatus of claim 8, further comprising a motor configured to tighten the strap, wherein the motor is operatively coupled to the controller, and wherein the controller includes logic that, when executed by the controller, causes the apparatus to perform operations including:
    clamping the finger with the strap to a sufficient pressure to measure the blood pressure pulsatility in the digital artery while not fully occluding the digital artery or an opposing digital artery of the finger.

10. The apparatus of claim 1, wherein the tactile sensor is positioned and oriented to measure the blood pressure pulsatility from an ulnar side digital artery of the finger.

11. The apparatus of claim 1, wherein the tactile sensor is adapted to measure blood pressure pulsatility by tonometry.

12. The apparatus of claim 1, wherein the apparatus is adapted to measure a left ventricular end diastolic pressure (LVEDP) or pulmonary capillary wedge pressure (PCWP), and wherein the apparatus further comprises an expiratory subsystem operatively coupled to the controller, the expiratory subsystem comprising:
    a mouthpiece shaped to receive an expiration of a user; and
    a pressure sensor coupled to the mouthpiece to measure an air pressure of the expiration, wherein the controller is coupled to the pressure sensor and adapted to monitor the air pressure while generating the pulsatility data.

13. The apparatus of claim 12, wherein the graphical user interface includes:
    an expiratory effort meter for displaying when a user is exerting appropriate expiratory effort; and
    a pulsatility meter for displaying when the blood pressure pulsatility is being sensed by the tactile sensor.

14. The apparatus of claim 12, wherein the pressure sensor is removably disposed within the housing and the mouthpiece is directly coupled to the housing.

15. The apparatus of claim 12, wherein the expiratory subsystem is removably coupleable to the housing.

16. The apparatus of claim 12, wherein the expiratory subsystem and the housing are shaped to removeably couple with a charging dock adapted to provide electrical power to power systems of each of the housing and the expiratory subsystem when coupled to the charging dock.

\* \* \* \* \*